United States Patent [19]

MacCoss et al.

[11] Patent Number: 4,579,849
[45] Date of Patent: Apr. 1, 1986

[54] N-ALKYLGUANINE ACYCLONUCLEOSIDES AS ANTIVIRAL AGENTS

[75] Inventors: Malcolm MacCoss, Freehold; Richard L. Tolman, Warren; Robert A. Strelitz, Edison, all of N.J.

[73] Assignee: Merck & Co., Inc., Rahway, N.J.

[21] Appl. No.: 597,785

[22] Filed: Apr. 6, 1984

[51] Int. Cl.$^4$ .................. C07D 473/18; A61K 31/52
[52] U.S. Cl. ................... 514/262; 544/276; 544/277
[58] Field of Search ............. 424/253; 544/276, 277; 514/262

[56] References Cited

U.S. PATENT DOCUMENTS

| 4,323,573 | 4/1982 | Schaeffer | 544/276 |
| 4,347,360 | 8/1982 | Ogilive | 544/276 |
| 4,461,757 | 7/1984 | Ogilive | 544/277 |

OTHER PUBLICATIONS

Weber, et al., J. Biol. Chem., vol. 251, No. 18, pp. 5657–5662 (1976), entitled "Inhibition of HeLa Cell Messenger RNA Translation by 7-Methylguanosine 5'-Monophosphate".

*Primary Examiner*—Nicholas S. Rizzo
*Attorney, Agent, or Firm*—Richard A. Elder; Hesna J. Pfeiffer; Julian S. Levitt

[57] ABSTRACT

Disclosed are compounds of the formula:

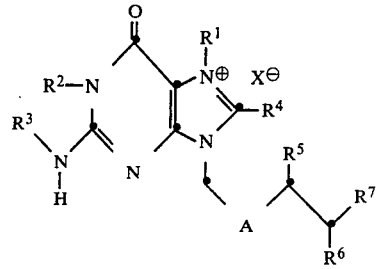

and the pharmaceutically acceptable salts thereof wherein $R^1$ and $R^2$ are independently alkyl, haloalkyl, alkenyl, haloalkenyl, alkynyl or haloalkynyl, each having 1 to 19 carbon atoms, or $R^2$ is hydrogen; $R^3$ is hydrogen, alkyl having 1 to 6 carbon atoms or hydroxyalkyl having 1 to 6 carbon atoms; $R^4$ is hydrogen, halogen, amino or alkyl having 1 to 4 carbon atoms; $R^5$, $R^6$ and $R^7$ are independently selected from hydrogen, hydroxy, alkyl having 1 to 6 carbon atoms, acyloxy having 1 to 8 carbon atoms, alkoxy having 1 to 6 carbon atoms, hydroxyalkyl having 1 to 6 carbon atoms, acyloxyalkyl having 1 to 12 carbon atoms, amino, alkylamino of 1 to 6 carbon atoms and $-PO_3=$, or two of $R^5$, $R^6$ and $R^7$ taken together form a group $-OPO_2O-$, $-CH_2OPO_2O-$, $-CH_2OPO_2OPO_2O=$, or $-OPO_2OPO_2O=$; A is O, S or $CH_2$ and X is a pharmaceutically acceptable anion. The compounds have antiviral activity, especially against viruses of the herpes class.

14 Claims, No Drawings

N-ALKYLGUANINE ACYCLONUCLEOSIDES AS ANTIVIRAL AGENTS

The present invention relates to N-alkylguanines. These compounds have antiviral activity. The compounds are particularly effective against herpes viruses, e.g. herpes simplex virus. The present invention also relates to processes for preparing said compounds, pharmaceutical compositions comprising said compounds and the treatment of viral infections in mammals with said compounds.

The compounds of the present invention may be represented by the formula:

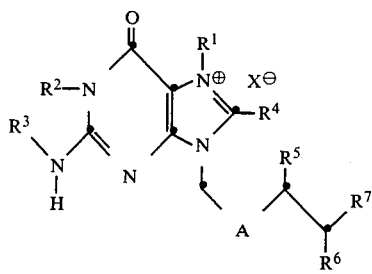

and the pharmaceutically acceptable salts thereof wherein $R^1$ and $R^2$ are independently alkyl, haloalkyl, alkenyl, haloalkenyl, alkynyl or haloalkynyl, each having 1 to 19 carbon atoms ($R^1$ is preferably alkyl or alkenyl and more preferably methyl), or $R^2$ is hydrogen; $R^3$ is hydrogen, alkyl having 1 to 6 carbon atoms or hydroxyalkyl having 1 to 6 carbon atoms; $R^4$ is hydrogen, halogen, amino or alkyl having 1 to 4 carbon atoms; $R^5$, $R^6$ and $R^7$ are independently selected from hydrogen, hydroxy, alkyl having 1 to 6 carbon atoms, acyloxy having 1 to 8 carbon atoms, alkoxy having 1 to 6 carbon atoms, hydroxyalkyl having 1 to 6 carbon atoms, acyloxyalkyl having 1 to 12 carbon atoms, amino, alkylamino having 1 to 6 carbon atoms and $-PO_3=$ or two of $R^5$, $R^6$ and $R^7$ taken together form a group $-OPO_2O-$, $-CH_2OPO_2O-$, $-CH_2OPO_2OPO_2O=$, or $-OPO_2OPO_2O=$; A is O, S or $CH_2$ and X is a pharmaceutically acceptable anion (preferably halide, alkanoate having 1 to 6 carbon atoms, alkylsulfonate having 1 to 6 carbon atoms, sulfate or phosphate). When the side chain at the 9-position on the guanine ring contains a strongly acidic monoanionic function (for example, a cyclic phosphate), that compound of the present invention will exist as a zwitterion, i.e, the compound will not require an accompanying anion. For example, the positive charge of the guaninium of 9-(2,2-dioxo-1,3,2-dioxaphosphorinan-5-yloxymethyl)-1,7-dimethylguanine is internally compensated for by the negative charge on the cyclic phosphate. The aforementioned alkyl groups, or the alkyl moieties of other groups, may be linear, branched or cyclic or may contain both cyclic and linear or cyclic and branched moieties. Halogen includes fluorine, chlorine, bromine and iodine.

Preferred compounds of the present invention are compounds of the formula I wherein $R^1$ and $R^2$ are methyl, $R^3$ and $R^4$ are H, $R^5$ is H or hydroxymethyl, $R^6$ is H and $R^7$ is hydroxyl or hydroxymethyl or, alternately, $R^5$ and $R^7$ taken together are $-CH_2OPO_2O-$.

The following are representative compounds of the present invention:

9-(1,3-Dihydroxy-2-propoxymethyl)-1,7-dimethylguaninium iodide;
9-(1,3-Dihydroxy-2-propoxymethyl)-1-methyl-7-ethylguaninium iodide;
9-(1,3-Dihydroxy-2-propoxymethyl)-1-ethyl-7-methylguaninium iodide;
9-(1,3-Dihydroxy-2-propoxymethyl)-1-propyl-7-methylguaninium iodide;
9-(1,3-Dihydroxy-2-propoxymethyl)-1-(prop-2-ynyl)-7-methyl-guaninium iodide;
9-(1,3-Diacetoxy-2-propoxymethyl)-1,7-dimethylguaninium iodide;
9-(1,3-Di-n-octanoyloxy-2-propoxymethyl)-1,7-dimethylguaninium iodide;
9-(1,3-Dihydroxy-2-propoxymethyl)-1-(prop-2-enyl)-7-methyl-guaninium iodide;
9-(1,3-Dihydroxy-2-propoxymethyl)-1,7-dimethylguaninium acetate;
9-(2,3-Dihydroxy-1-propoxymethyl)-1,7-dimethylguaninium iodide;
9-(2-Hydroxyethoxymethyl)-1,7-dimethylguaninium iodide;
9-(4-Hydroxybutyl)-1,7-dimethylguaninium iodide;
9-(4-Hydroxy-3-hydroxymethylbutyl)-1,7-dimethylguaninium iodide;
9-(2-hydroxy-1,3,2-dioxaphosphorinan-5-yloxymethyl)-1,7-dimethylguanine P-oxide;
9-(1,3-Dihydroxy-2-propoxymethyl)-1-methyl-7-(prop-2-enyl)guaninium iodide;
9-(1,3-Dihydroxy-2-propoxymethyl)-1-methyl-7-(prop-2-ynyl)guaninium iodide;
9-(1,3-Dihydroxy-2-propoxymethyl)-1-methyl-7-(3-methylbut-2-enyl)guaninium iodide;
9-(1,3-Dihydroxy-2-propoxymethyl)-1-methyl-7-(hex-2-enyl)guaninium iodide;
9-(1,3-Dihydroxy-2-propoxymethyl)-1-methyl-7-(but-3-ynyl)guaninium iodide;
9-(1,3-Dihydroxy-2-propoxymethyl)-1-methyl-7-ethynylguaninium iodide;
9-(1,3-Dihydroxy-2-propoxymethyl)-1-methyl-7-hexadecylguaninium iodide;
9-(1,3-Dihydroxy-2-propoxymethyl)-1-methyl-7-(oct-7-ynyl)guaninium iodide;
9-(2-Hydroxyethoxymethyl)-1-ethyl-7-methylguaninium chloride;
9-(2-Hydroxyethoxymethyl)-1-propyl-7-methylguaninium chloride;
9-(2-Hydroxyethoxymethyl)-1-ethenyl-7-methylguaninium chloride;
9-(2-Hydroxyethoxymethyl)-1-(prop-2-ynyl)-7-methylguaninium chloride;
9-(4-Hydroxybutyl)-1,7-dimethyl-8-aminoguaninium propanoate;
9-(4-Hydroxybutyl)-1,7-dimethyl-8-bromoguaninium propanoate;
9-(4-Hydroxybutyl)-1,7-dimethyl-8-chloroguaninium propanoate;
9-(4-Hydroxybutyl)-1,7,8-trimethyl-guaninium propanoate;
9-(4-Hydroxybutyl)-1,7-dimethyl-$N^2$-(2-hydroxyethyl)-guaninium propanoate;
9-(4-Hydroxybutyl)-1,7-dimethyl-$N^2$-(2,3-dihydroxypropyl)guaninium propanoate;
9-(3,4-Dihydroxybutyl)-1,7-dimethylguaninium ethylsulfonate;
9-(3-Hydroxypropyloxymethyl)-1,7-dimethylguaninium ethylsulfonate;

9-(2-Hydroxyethylthiomethyl)-1,7-dimethylguaninium ethylsulfonate;
9-(2,4-Dihydroxy-1,3,5,2,4-trioxadiphosphepan-6-yloxymethyl)-1,7-dimethylguanine ethylsulfonate P,P'-dioxide;
9-(2,4-Dihydroxy-1,3,5,2,4-trioxadiphosphacan-7-yloxymethyl)-1,7-dimethylguanine ethylsulfonate P,P'-dioxide;
9-(1-Hydroxy-3-methoxy-2-propoxymethyl)-1,7-dimethylguaninium phosphate;
9-(1-Hydroxy-3-methylamino-2-propoxymethyl)-1,7-dimethylguaninium phosphate; and
9-(1-Hydroxy-3-phosphoryloxy-2-propoxymethyl)-1,7-dimethylguanine.

The following compounds are preferred:
9-(1,3-Dihydroxy-2-propoxymethyl)-1,7-dimethylguaninium iodide;
9-(1,3-Dihydroxy-2-propoxymethyl)-1-methyl-7-ethylguaninium iodide;
9-(1,3-Dihydroxy-2-propoxymethyl)-1-ethyl-7-methylguaninium iodide;
9-(1,3-Dihydroxy-2-propoxymethyl)-1,7-dimethylguaninium acetate;
9-(4-Hydroxybutyl)-1,7-dimethylguaninium iodide;
9-(4-Hydroxy-3-hydroxymethylbutyl)-1,7-dimethylguaninium iodide;
9-(2-Hydroxy-1,3,2-dioxaphosphorinan-5-yloxymethyl)-1,7-dimethylguanine P-oxide; and
9-(1,3-Di-n-octanoyloxy-2-propoxymethyl)-1,7-dimethylguaninium iodide.

The compounds of the present invention may be prepared as shown in the following scheme:

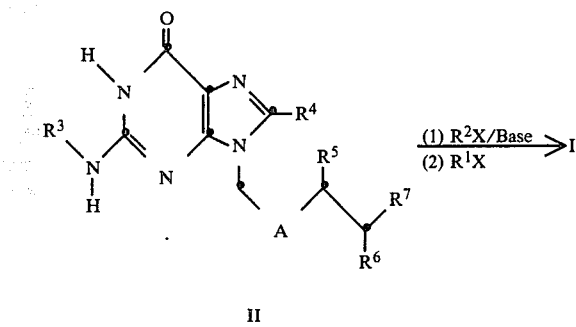

II

As shown above, Compound II is alkylated at $N^1$ with a suitable alkylating agent (e.g. an alkyl halide) in the presence of one equivalent of base (e.g. NaH or $K_2CO_3$). This is followed by alkylation at $N^7$ at or near neutral pH with a suitable alkylating agent such as an alkyl halide. Also, dialkylation can be achieved by alkylation at $N^7$, first under neutral conditions, followed by alkylation at $N^1$ after the addition of 2 equivalents of base. If $R^1$ and $R^2$ are identical, dialkylation may be carried out in a single step by reacting with two equivalents of a suitable alkylating agent (such as an alkyl halide) in the presence of base.

The above procedure is applicable to a wide range of substituted acyclonucleosides. For example, 2- and 8-substituted guanines are readily available by procedures known to those skilled in the art. Similarly, N-substituted guanines are readily available from protected guanines by general procedures employing various types of acyclonucleoside side chains.

For example, U.S. Ser. No. 574,113, filed Jan. 26, 1984, discloses an acyclonucleoside with a 4-hydroxy-3-hydroxymethylbutyl side chain. Also, using a preformed, protected, guanine acyclonucleoside, selective tosylation of hydroxyl groups on the side chain may be effected and nucleophilic displacement with substituted amines or alkoxides furnishes alkylamino or alkoxy substituted guanine acyclonucleosides. In addition, U.S. Ser. No. 533,676, filed Sept. 19, 1983, discloses cyclic pyrophosphates of purine acyclonucleosides. 2- and 8-haloguanine acyclonucleosides are readily available by acyclonucleoside synthesis using preformed halopurines or, in the case of 8-substitution, the halogen can also be introduced directly by electrophilic substitution. Other 8-substituted guanine acyclonucleosides are prepared by nucleophilic substitution of 8-halo guanine derivatives, for example 8-amino, or by introduction of the 8-substituent into the purine moiety before alkylation by the side chain intermediate.

Pharmaceutically acceptable salts of the compound of the present invention may be prepared by ion-exchange chromatography from an appropriate salt (for example, the iodide, chloride or acetate salt) and the appropriate anion-exchange resin.

In another aspect of the invention there is provided a pharmaceutical composition or preparation comprising a compound of the formula I, or a pharmaceutically acceptable salt thereof, together with a pharmaceutically acceptable carrier therefor. In a particular aspect the pharmaceutical composition comprises a compound of the present invention in effective unit dosage form.

As used herein the term "effective unit dosage" or "effective unit dose" is denoted to mean a predetermined antiviral amount sufficient to be effective against the virus in vivo. Pharmaceutically acceptable carriers are materials useful for the purpose of administering the medicament, and may be solid, liquid or gaseous materials, which are otherwise inert and medically acceptable and are compatible with the active ingredients.

These pharmaceutical compositions may be given parenterally, orally, used as a suppository or pessary, applied topically as an ointment, cream, aerosol, powder, or given as eye or nose drops, etc., depending on whether the preparation is used to treat internal or external viral infections.

For internal infections the compositions are administered orally or parenterally at dose levels of about 0.1 to 250 mg per kg, preferably 1.0 to 50 mg per kg of mammal body weight, and are used in man in a unit dosage form, administered, e.g. a few times daily, in the amount of 1 to 250 mg per unit dose.

For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavoring, preserving, suspending, thickening or emulsifying agents may be included. Tablets and granules are preferred, and these may be coated.

For parenteral administration or for administration as drops, as for eye infections, the compounds may be presented in aqueous solution in a concentration of from about 0.1 to 10%, more preferably 0.1 to 7%, most preferably 0.2% w/v. The solution may contain antioxidants, buffers, etc.

Alternatively, for infections of the eye, or other external tissues, e.g. mouth and skin, the compositions are preferably applied to the infected part of the body of the patient as a topical ointment or cream. The compounds may be presented in an ointment, for instance, with a water soluble ointment base, or in a cream, for instance with an oil in water cream base, in a concentration of from about 0.1 to 10%, preferably 0.1 to 7%, most preferably 1% w/v.

The compounds of the present invention may also be administered in combination with other antiviral drugs such as acyclovir. Because the compounds of the present invention are not converted to the corresponding triphosphate in virus-infected cells and conversion to the triphosphate is not important for expression of antiviral activity as are other nucleoside antiviral agents, the compounds of the present invention will form synergistic combinations with other antiviral agents.

The following examples illustrate the present invention without, however, limiting the same thereto. All temperatures are expressed in degrees Celsius.

EXAMPLE 1

1-Methyl-9-(1,3-dihydroxy-2-propoxymethyl)guanine

To a stirred solution of 9-(1,3-dihydroxy-2-propoxymethyl)guanine (510.4 mg, 2.0 mmol) in sieve-dried DMSO (dimethylsulfoxide) (4 ml), under $N_2$, was added 80 mg of 60% NaH in oil (i.e. 48 mg of NaH, 2.0 mmol). Effervescence was observed and after 10 minutes a clear solution was obtained. Methyl iodide (312 mg, 2.20 mmol) in dry DMSO (dimethylsulfoxide) (1 ml) was added in 3 portions over a period of 5 minutes. After stirring overnight at room temperature the reaction mixture was poured into $CH_2Cl_2$ (200 ml) and the precipitate so formed was filtered off. This was dissolved in 15 ml of MeOH—$H_2O$ (1:4) and applied to an ion-exchange column of Dowex 1×2 (OH$^-$form, 3.5×18.5 cm) packed in the same solvent. The column was developed with MeOH—$H_2O$ (1:4) and fractions containing the required product were pooled and evaporated to dryness. The white powder so obtained (350 mg, 1.30 mmol; 65%) had a melting point of 222°–222.5° C. and was analytically pure.

Anal.: Calcd. for $C_{10}H_{15}N_5O_4$: C, 44.61; H, 5.62; N, 26.01. Found: C, 44.23; H, 5.64; N, 25.69.

UV (MeOH): λ max 255 nm ($\epsilon=10,320$), shoulder 270 nm; (0.01 M HCl): λ max 255 nm ($\epsilon=9,200$), shoulder 270 nm; (0.01 M NaOH): λ max 252 nm ($\epsilon=10,000$), shoulder 265 nm. $^{13}$CMR and PMR were in agreement with the structure.

EXAMPLE 2

1-Ethyl-9-(1,3-dihydroxy-2-propoxymethyl)guanine

To a stirred solution of 9-(1,3-dihydroxy-2-propoxymethyl)guanine (766 mg, 3.0 mmol) in sieve-dried DMSO (4 ml), under $N_2$, was added 120 mg of 60% NaH in oil (i.e. 72 mg NaH, 3.0 mmol). Hydrogen evolution ceased and a clear solution was obtained after 10 minutes. Ethyl iodide (491 mg, 3.15 mmol) in DMSO (1 ml) was added over approximately 1 minute. The reaction was stirred overnight and then poured into $CH_2Cl_2$. The gummy precipitate was filtered off and triturated under methanol to give crystalline material. This was dissolved in MeOH—$H_2O$ (2:3) and applied to a Dowex 1×2 column (OH$^-$form, 100 ml) packed in the same solvent. The column was developed in MeOH—$H_2O$ (2:3) and fractions containing the required product were pooled and evaporated to dryness. This residue was crystallized from methanol to give 230 mg (27% yield) of product.

Anal. Calcd. for $C_{11}H_{17}N_5O_4$: C, 46.64; H, 6.05; N, 24.72. Found: C, 46.82; H, 6.07; N, 24.84.

UV (MeOH): λ max 257 nm ($\epsilon=13,000$), shoulder 270 nm; shoulder 275 nm; (0.01 M HCl): λ max 257 nm ($\epsilon=11,074$), shoulder 275 nm; (0.01 M NaOH): λ max 255 nm ($\epsilon=12,230$), shoulder 270 nm; $^{13}$CMR and PMR were in agreement with the structure.

EXAMPLE 3

1-n-Propyl-9-(1,3-dihydroxy-2-propoxymethyl)guanine 9-(1,3-Dihydroxy-2-propoxymethyl)guanine (766 mg, 3.0 mmol) and 120 mg of 60% NaH in oil (i.e. 72 mg of NaH, 3.0 mmol) were stirred vigorously under $N_2$ with dry DMSO (4 ml). After the evolution of $H_2$ had ceased and a clear solution was obtained, n-propyl iodide (535 mg, 3.15 mmol) was added and the reaction was stirred overnight at room temperature. The mixture was then poured into $CH_2Cl_2$ (250 ml) and a gummy precipitate was formed which was filtered off after standing for 1 hour. This was taken up in aqueous MeOH and the precipitate so formed (unreacted 9-(1,3-dihydroxy-2-propoxymethyl)guanine, 115 mg) was filtered off. The filtrate was concentrated to an oil and applied to a Dowex 1×2 column (OH$^-$form) packed in MeOH—$H_2O$ (15:85). The column was developed first in MeOH—$H_2O$ (15:85) and then with MeOH—$H_2O$ (3:7) and fractions containing the required product were pooled and evaporated to dryness to give 31% overall yield of product. Analytically pure material was obtained by crystallization from 2-propanol-MeOH.

Anal.: Calcd for $C_{12}H_{19}N_5O_4$ 0.8 $H_2O$: C, 46.23; H, 6.66; N, 22.4. Found: C, 46.55; H, 6.53; N, 23.34.

UV (MeOH): λ max 257 nm ($\epsilon=14,280$), shoulder 270 nm; (0.01M HCl): λ max 257 nm ($\epsilon=12,000$), shoulder 275 nm; (0.01 M NaOH): λ max 255 nm ($\epsilon=13,270$), shoulder 270 nm; $^{13}$CMR and PMR were in agreement with the structure.

EXAMPLE 4

7-Methyl-9-(1,3-dihydroxy-2-propoxymethyl)guanine iodide

To a stirred solution of 9-(1,3-dihydroxy-2-propoxymethyl)guanine (510 mg, 2.0 mmol) in sieve-dried DMF (dimethylformamide) (50 ml) was added a solution of methyl iodide (305 mg; 2.15 mmol) in dry DMF (2 ml). After stirring at room temperature for 5 hours, little reaction was apparent by TLC (thin layer chromatography) evaluation and the reaction was heated at 60° under a reflux condenser overnight. TLC then indicated complete reaction and the mixture was cooled and evaporated to dryness, giving an oil. This was evaporated twice to dryness from MeOH and a crystalline product was obtained. This material was recrystallized from MeOH (25 ml) and the product was filtered after standing 3 days at ambient temperature. The yield was 260 mg (0.65 mmol, 33%). An analytical sample was obtained by recrystallization from absolute EtOH.

Anal.: Calcd for $C_{10}H_{16}N_5O_4I$: C, 30.24; H, 4.06; N, 17.63. Found: C, 30.65; H, 4.13; N, 17.53.

UV (MeOH): λmax 222 nm ($\epsilon=22,880$), 255 nm ($\epsilon=6,100$), 283 nm ($\epsilon=6,390$); (0.01M HCl): λmax 256 nm ($\epsilon=10,490$), shoulder 275 nm. $^{13}$CMR and PMR were in agreement with the structure.

EXAMPLE 5

1-Ethyl-7-methyl-9-(1,3-dihydroxy-2-propoxymethyl) guanine iodide

1-Ethyl-9-(1,3-dihydroxy-2-propoxymethyl) guanine (259 mg, 0.91 mmol) and methyl iodide (142 mg, 1.0 mmole) were dissolved in dry DMF (3 ml) and heated at 50° overnight. The reaction mixture was poured into $CH_2Cl_2$ (230 ml) to give a cloudy solution which deposited solid on the walls of the flask after standing for 5 hours at 4°. The liquid was decanted off and the solid was triturated under $CH_2Cl_2$ and then removed by centrifugation to give 261 mg of crude product. This was recrystallized from MeOH to give 156 mg (54% yield) of analytically pure material having a melting point of 148°–150°.

Anal.: Calcd for $C_{12}H_{20}N_5O_4I_1$: C, 33.89; H, 4.74; N, 16.47. Found: C, 33.99; H, 4.75; N, 16.37.

UV (MeOH): $\lambda$max 262 nm ($\epsilon = 10,880$), shoulder 280 nm; (0.01 M HCl): $\lambda$max 259 nm ($\epsilon = 10,000$), shoulder 277 nm; $^{13}$CMR and PMR were in agreement with the structure.

EXAMPLE 6

1-Propyl-7-methyl-9-(1,3-dihydroxy-2-propoxymethyl)guanine iodide

Following the method of Example 5, using 1-propyl-9-(1,3-dihydroxy-2-propoxymethyl)guanine and methyl iodide in DMF at 60° C. overnight, prepare 1-propyl-7-methyl-9(1,3-dihydroxypropoxymethyl)guanine iodide.

EXAMPLE 7

1,7-Dimethyl-9-(1,3-dihydroxy-2-propoxymethyl)guanine iodide

Method A:

To a stirred mixture of 9-(1,3-dihydroxy-2-propoxymethyl)guanine (1.0 g, 3.92 mmol) and dried $K_2CO_3$ (1.0 g) in dry DMSO (4 ml) was added a solution of methyl iodide (1.0 g, 7.05 mmol) in dry DMSO (2 ml). The dropwise addition took 5 minutes. The reaction mixture was stirred at room temperature for 5 hours, filtered through Celite (diatomaceous earth) and was then poured into $CH_2Cl_2$ (200 ml). The white solid so obtained (1.6 g) was recrystallized from MeOH (50 ml) and the product was filtered after standing overnight in the refrigerator (0.8 g, 1.95 mmol, 50%). A second recrystallization from MeOH was necessary to remove minute traces of starting material.

Melting point: sample softens at 165°–170°, turns brown at 220°–225° and finally melts with decomposition at 260°–262°.

Anal.: Calcd. for $C_{11}H_{18}N_5O_4I$: C, 32.13; H, 4.41; N, 17.03. Found: C, 31.99; H, 4.36; N, 16.98.

UV (MeOH): $\lambda$max 261 nm ($\epsilon = 10,690$), shoulder 275 nm; (0.01 M HCl): $\lambda$max 258 nm ($\epsilon = 12,130$). $^{13}$CMR and PMR were in agreement with the structure.

Method B:

1-Methyl-9-(1,3-dihydroxy-2-propoxymethyl) guanine (164 mg; 0.61 mmol) and methyl iodide (100 mg, 0.7 mmol) were mixed with dry DMF (5 ml) and heated to 70° in a pressure bottle for 8 hours. The mixture was concentrated to an oil and $CH_2Cl_2$ was added. A precipitate formed after trituration which was removed by centrifigation. This solid was crystallized from MeOH to give material identical to that prepared from Methods A and C.

Method C:

7-Methyl-9-(1,3-dihydroxy-2-propoxymethyl) guanine iodide (300 mg, 0.76 mmol), methyl iodide (216 mg, 1.52 mmol) and dry $K_2CO_3$ (126 mg, 0.91 mmol) were stirred in dry DMSO (5 ml) at room temperature for 4 hours. The reaction was filtered and concentrated to an oil which was triturated under $CH_2Cl_2$ (40 ml) to give a white precipitate. This crude product was crystallized from MeOH to give 160 mg of product identical to material prepared by Methods A and B.

EXAMPLE 8

1-Methyl-9-(2-hydroxyethoxymethyl)guanine

To a stirred solution of 9-(2-hydroxyethoxymethyl)guanine (500 mg; 2.22 mmol) in sieve-dried DMSO (4 ml), under $N_2$, was added 98 mg of 60% NaH in oil (i.e. 58.8 mg of NaH, 2.45 mmol). After the evolution of $H_2$ had ceased, a clear solution was obtained after 15 minutes. Methyl iodide (315 mg, 2.22 mmol) in dry DMSO (1.5 ml) was added over a period of about 1 minute and the reaction mixture was stirred under $N_2$ at room temperature overnight. The mixture was added to $CH_2Cl_2$ (200 ml) and the crude product formed a gum. The supernatant was decanted (some solid material was filtered and then mixed back with the gum) and the gum was dissolved in 20 ml of MeOH—$H_2O$ (1:4) and applied to an ion-exchange column of Dowex 1×2 (OH$^-$ form, 3.5×19 cm) packed in the same solvent. The column was developed with MeOH—$H_2O$ (1:4) and fractions containing the required product were pooled and evaporated to dryness (yield, 250 mg, 1.05 mmol, 47%). This material was crystallized from MeOH (about 150 ml) to give 201 mg of analytically pure material having a melting point of 235°–236°.

Anal.: Calcd. for $C_9H_{13}N_5O_3$: C, 45.18; H, 5.48; N, 29.28. Found: C, 45.10; H, 5.48; N, 29.04.

UV (MeOH): $\lambda$ max 256.5 nm ($\epsilon = 11,310$); (0.01 M HCl): $\lambda$ max 256.5 nm ($\epsilon = 10,660$); (0.01 M NaOH): $\lambda$ max 254.5 nm ($\epsilon = 11,200$). $^{13}$CMR and PMR were in agreement with the structure.

EXAMPLE 9

7-Methyl-9-(2-hydroxyethoxymethyl)guanine iodide

To a stirred solution of 9-(2-hydroxyethoxymethyl)guanine (1.0 g; 4.44 mmol) in dry DMF (50 ml) was added a solution of methyl iodide (680 mg, 4.77 mmol) in dry DMF (2 ml). This mixture was heated under a reflux condenser under $N_2$ at 57° C. overnight. The mixture was concentrated in vacuo to an oil and the evaporation was repeated several times from MeOH. The residue was dissolved in MeOH (20 ml) and 2-propanol (150 ml) was added and the mixture was stirred overnight. A yellow solid was obtained which was filtered off (200 mg). This was recrystallized from MeOH (25 ml) (solution filtered through a little charcoal). Crystallization was induced by concentration of the solution, cooling and by the addition of a little 2-propanol.

EXAMPLE 10

1,7-Dimethyl-9-(2-hydroxyethoxymethyl)guanine iodide 1.0 g (4.44 mmole) of 9-(2-hydroxyethoxymethyl)guanine was dissolved in sieve-dried DMSO (4 ml) and anhydrous $K_2CO_3$ (1.35 g; 9.77 mmol) was added. To this stirred mixture was added methyl iodide (1.40 g; 9.86 mmol) in dry DMSO (2 ml) over a 15 minute period. After stirring overnight at room temperature, the mixture was filtered through a Celite pad. The filtrate was diluted to 400 ml with $CH_2Cl_2$ and the white precipitate so formed was filtered off to give the crude product. This was recrystallized twice from MeOH to give 711 mg of pure product (42%) with a melting point of 255°–256° (decomp.; softens at 240°–250°).

Anal.: Calcd. for $C_{10}H_{16}N_5O_5I$: C, 31.51; H, 4.23; N, 18.37. Found: C, 31.49; H, 4.21; N, 18.17.

UV (MeOH): $\lambda$max 262 nm ($\epsilon = 12,310$), shoulder 280 L 20 nm; (0.01M HCl): $\lambda$max 258 nm ($\epsilon = 11,370$), shoulder 275 nm.

$^{13}$CMR and PMR were in agreement with the structure.

EXAMPLE 11

(S)-1,7-Dimethyl-9-(2,3-dihydroxy-1-propoxymethyl)-guanine iodide 0.500 g (1.96 mmol) of (S)-9-(2,3-dihydroxy-propoxymethyl)guanine was dissolved in sieve-dried DMSO (4 ml) and powdered anhydrous $K_2CO_3$ (0.677 g; 4.9 mmol) was added. To this stirred mixture was added methyl iodide (0.700 g; 4.9 mmol) in dry DMSO (2 ml) in one portion. After stirring overnight at room temperature, the reaction mixture was filtered through a Celite pad, washing with 2 ml of DMSO. The filtrate was diluted with $CH_2Cl_2$ (400 ml) and the white precipitate so formed was filtered off after standing at room temperature. The product was recrystallized from 10 ml MeOH (filtered after chilling to 4°) to give 0.42 g of product having a melting point of 143°–145° (decomp.).

UV (MeOH): $\lambda$max 261 nm ($\epsilon = 11,990$), shoulder 280 nm; (0.01 M HCl): $\lambda$max 258 nm ($\epsilon = 11,140$), shoulder 275 nm.

$^{13}$CMR and PMR were in agreement with the structure.

Anal.: Calcd. for $C_{11}H_{18}N_5O_4I \cdot 0.6H_2O$: C, 31.31; H, 4.56; N, 16.60. Found: C, 31.62; H, 4.48; N, 16.17.

EXAMPLE 12

1-Methyl-9-(1,3-dioctanoyloxy-2-propoxymethyl)guanine

1-Methyl-9-(1,3-dihydroxy-2-propoxymethyl) guanine (340 mg, 1.26 mmol) was suspended in dry DMF and dry pyridine (approximately 20 ml total) and evaporated to dryness. This process was repeated twice, the final time concentrating the suspension down to 10 ml. This suspension was cooled to 0°, under $N_2$, and a solution of octanoyl chloride (822 mg, 5.05 mmol) in dry DMF (1 ml) was added. This reaction was stirred overnight at room temperature. Methylene chloride was then added and the mixture was extracted with saturated aqueous $NaHCO_3$ solution. The organic phase was then washed three times with $H_2O$, dried over $MgSO_4$, filtered and evaporated to dryness. The residual oil was dissolved in $CH_2Cl_2$ and applied to a column of silica gel, packed in $CH_2Cl_2$. Elution was first performed with $CH_2Cl_2$ followed by 1% MeOH in $CH_2Cl_2$ (200 ml), 2% MeOH in $CH_2Cl_2$ (200 ml), 3% MeOH in $CH_2Cl_2$ (100 ml) and finally 5% MeOH in $CH_2Cl_2$ (100 ml). Fractions containing the required product were pooled and evaporated to dryness to give 529 mg of product. It was recrystallized from ether/petroleum ether. The PMR spectrum was in accord with the structure.

Anal. Calcd. for $C_{26}H_{43}N_5O_6$: C, 59.86; H, 8.31; N, 13.43. Found: C, 59.86; H, 8.27; N, 13.51.

UV(MeOH): $\lambda$max 257 nm ($\epsilon = 12,860$), shoulder 269 nm.

EXAMPLE 13

1,7-Dimethyl-9-(1,3-dioctanoyloxy-2-propoxymethyl) guanine iodide

Method A:

9-(1,3-dioctanoyloxy-2-propoxymethyl)guanine (200 mg, 0.394 mmol) and anhydrous $K_2CO_3$ (114 mg, 0.827 mmol) were mixed in dry DMSO (2 ml) and stirred at room temperature. To this mixture was added methyl iodide (117 mg, 0.827 mmol) and the reaction was heated at 50° overnight. Additional methyl iodide (excess) was then added and the mixture was heated at 70° in a pressure tube overnight. The reaction mixture was filtered, evaporated to dryness and the residue was dissolved in $CHCl_3$ and applied to a silica gel column. The column was developed first with $CHCl_3$—MeOH—$H_2O$ (95:5:0.5) and then with $CHCl_3$—MeOH—$H_2O$ (90:10:1). Fractions containing the required product were pooled and evaporated to dryness to give 50 mg of chromatographically pure product. This residue was partitioned between $CHCl_3$ and $H_2O$ and the organic phase was dried over $MgSO_4$, filtered and evaporated to dryness. The residue was crystallized from $CHCl_3$-ethyl ether to give 26 mg of analytically pure product.

Anal.: Calcd. for $C_{27}H_{46}N_5O_6I$: C, 48.86; H, 6.98; N, 10.55. Found: C, 48.91; H, 7.03; N, 10.51.

UV(MeOH): $\lambda$max 262 nm($\epsilon = 10,830$), shoulder 280 nm.

Method B:

1-Methyl-9-(1,3-dioctanoyloxy-2-propoxymethyl) guanine (410 mg, 0.79 mmol) and methyl iodide (227 mg, 1.6 mmol) were mixed in dry DMF (4 ml) and stirred in a pressure vessel at 70° for 6 hours. The reaction mixture was evaporated to dryness and the oil so formed was dissolved in $CHCl_3$ and ethyl ether was added by diffusion. Slightly colored product (430 mg, 82% yield) was obtained which was recrystallized to give material identical to that prepared by Method A.

EXAMPLE 14

7-Methyl-9-(1,3-dihydroxy-2-propoxymethyl)guanine cyclic monophosphate

See C. B. Reese and J. E. Sulston, Biochem. Biophys Acta 149, 293 (1967) who use a similar method for methylation of guanine-containing dinucleotides.

9-(1,3-Dihydroxy-2-propoxymethl)guanine cyclic monophosphate, sodium salt (0.45 mmol) is dissolved in $H_2O$ (75 ml) and to the stirred solution is added dimethyl sulfate (2.0 g). The pH is maintained at 5.5 by the dropwise addition of 0.5 M aqueous KOH. After 2 hours, an additional 2.0 g of dimethyl sulfate is added and after a further 6 hours of reaction the solution is extracted with $Et_2O$ (2 × 100 ml) and the aqueous phase is concentrated to small volume. This is then applied to a Dowex 1×2 (Cl−form) ion-exchange column, packed and developed in $H_2O$. The product is eluted just after the solvent front and fractions containing the title compound are pooled and evaporated to dryness. This material is dissolved in a little $H_2O$ and lyophilized to give the product as a white powder.

EXAMPLE 15

1,7-Dimethyl-9-(1,3-dihydroxy-2-propoxymethyl)guanine cyclic monophosphate

Method A:

9-(1,3-Dihydroxy-2-propoxymethyl)guanine cyclic monophosphate, sodium salt is methylated in DMSO in the presence of $K_2CO_3$ (3.5 molar equivalents) and methyl iodide (3.5 molar equivalents) as described in Example 7 (Method A). The crude phosphotriester product is hydrolyzed with dilute acid and the title compound is purified by passage down a Dowex 1×2 ($Cl^-$ form) ion-exchange column as described in Example 14.

Method B:

1-Methyl-9-(1,3-dihydroxy-2-propoxymethyl)guanine cyclic monophosphate, sodium salt is methylated in $H_2O$ with dimethyl sulfate as described in Example 14 to give 1,7-dimethyl-9-(1,3-dihydroxy-2-propoxymethyl)guanine cyclic monophosphate.

EXAMPLE 16

Oil in Water Cream Base

| | |
|---|---|
| (S)—1,7-dimethyl-9-(2,3-dihydroxy-1-propoxymethyl)guanine iodide | 5.0 g |
| Lanolin, Anhydrous | 20.0 g |
| Polysorbate 60 | 4.0 g |
| Sorbitan Monopalmitate | 2.0 g |
| Light Liquid Paraffin | 4.0 g |
| Propylene Glycol | 5.0 g |
| Methyl Hydroxybenzoate | 0.1 g |
| Purified Water to | 100.0 g |

EXAMPLE 17

Water Soluble Ointment Base

| | |
|---|---|
| (S)—1,7-dimethyl-9-(2,3-dihydroxy-1-propoxymethyl)guanine iodide | 0.5 g |
| Glycerol | 15.0 g |
| Macrogol 300 | 20.0 g |
| Polyethylene Glycol 1500 | 64.5 g |

EXAMPLE 18

Tablet—(Total weiqht 359 mg)

| | |
|---|---|
| (S)—1,7-dimethyl-9-(2,3-dihydroxy-1-propoxymethyl)guanine iodide | 100 mg |
| Lactose | 200 mg |
| Starch | 50 mg |
| Polyvinylpyrrolidone | 5 mg |
| Magnesium Stearate | 4 mg |

For each of Examples 16–18, combine the listed ingredients by standard techniques. Similarly prepare other compositions of the present invention by substituting other compounds of the invention (e.g. others of the preferred compounds disclosed on page 6) for (S)-1,7-dimethyl-9-(2,3-dihydroxy-1-propoxymethyl)guanine iodide.

What is claimed is:

1. A compound of the formula:

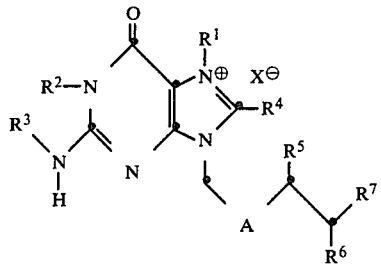

wherein $R^1$ and $R^2$ are independently alkyl or haloalkyl, each having 1 to 12 carbon atoms or alkenyl, haloalkenyl, alkynyl or haloalkynyl, each having 2 to 12 carbon atoms, or $R^2$ is hydrogen; $R^3$ is hydrogen, alkyl having 1 to 6 carbon atoms or hydroxyalkyl having 1 to 6 carbon atoms; $R^4$ is hydrogen, halogen, amino or alkyl having 1 to 4 carbon atoms; $R^5$, $R^6$ and $R^7$ are independently selected from hydrogen, hydroxy, alkyl having 1 to 6 carbon atoms, acyloxy having 1 to 8 carbon atoms, alkoxy having 1 to 6 carbon atoms, hydroxyalkyl having 1 to 6 carbon atoms, acyloxyalkyl having 1 to 12 carbon atoms, amino, alkylamino having 1 to 6 carbon atoms and $—PO_3^=$ or two of $R^5$, $R^6$ and $R^7$ taken together form a group $—OPO_2O^-—$, $—CH_2OPO_2O^-—$, $—CH_2OPO_2OPO_2O^=—$, or $—OPO_2OPO_2O^=—$; A is O, S or $CH_2$ and X is a pharmaceutically acceptable anion from the group consisting of fluoride, chloride, bromide, iodide, alkanoate having 1 to 6 carbon atoms, alkylsulfonate having 1 to 6 carbon atoms, sulfate and phosphate.

2. A compound according to claim 1, wherein $R^1$ is alkyl or alkenyl.

3. A compound according to claim 1, wherein $R^1$ and $R^2$ are methyl, $R^3$ and $R^4$ are H, $R^5$ is H or hydroxymethyl, $R^6$ is H and $R^7$ is hydroxyl or hydroxymethyl or, alternately, $R^5$ and $R^7$ taken together are $—CH_2OPO_2O^-—$.

4. 9-(1,3-Dihydroxy-2-propoxymethyl)-1,7-dimethylguaninium iodide, according to claim 1.

5. 9-(1,3-Dihydroxy-2-propoxymethyl)-1-methyl-7-ethylguaninium iodide, according to claim 1.

6. 9-(1,3-Dihydroxy-2-propoxymethyl)-1-ethyl-7-methylguaninium iodide, according to claim 1.

7. 9-(1,3-Dihydroxy-2-propoxymethyl)-1,7-dimethylguaninium acetate, according to claim 1.

8. 9-(2,3-Dihydroxy-1-propoxymethyl)-1,7-dimethylguaninium iodide, according to claim 1.

9. 9-(2-Hydroxyethoxymethyl)-1,7-dimethylguaninium iodide, according to claim 1.

10. 9-(4-Hydroxybutyl)-1,7-dimethylguaninium iodide, according to claim 1.

11. 9-(4-Hydroxy-3-hydroxymethylbutyl)-1,7-dimethylguaninium iodide, according to claim 1.

12. 9-(2,2-dioxo-1,3,2-dioxaphosphorinan-5-yloxymethyl)-1,7-dimethylguanine, according to claim 1.

13. An antiviral pharmaceutical composition comprising an effective amount of a compound of claim 1 and a pharmaceutically acceptable carrier.

14. A method of treating viral infections in mammals comprising administering to patient in need of such treatment an effective amount of a compound according to claim 1.

* * * * *